United States Patent [19]

Arena

[11] Patent Number: 4,510,339

[45] Date of Patent: Apr. 9, 1985

[54] INCREASING CATALYST LIFETIME IN HYDROGENATION OF A CARBOHYDRATE IN AQUEOUS SOLUTION

[75] Inventor: Blaise J. Arena, Des Plaines, Ill.

[73] Assignee: UOP Inc., Des Plaines, Ill.

[21] Appl. No.: 629,151

[22] Filed: Jul. 9, 1984

Related U.S. Application Data

[63] Continuation-in-part of Ser. No. 457,546, Jan. 12, 1983, abandoned.

[51] Int. Cl.$^3$ .................. C07C 29/136; C07C 29/14; C07C 31/18; C07C 31/26
[52] U.S. Cl. .................................................. 568/863
[58] Field of Search .......................................... 568/863

[56] References Cited

U.S. PATENT DOCUMENTS

| | | | |
|---|---|---|---|
| 2,174,651 | 10/1939 | Byrkit | 260/100 |
| 2,879,307 | 3/1959 | Von Bezard et al. | 260/635 |
| 3,963,788 | 6/1976 | Kruse et al. | 260/635 |

Primary Examiner—J. E. Evans
Attorney, Agent, or Firm—William H. Page, II; Eugene I. Snyder

[57] ABSTRACT

Improved lifetimes of group VIII metals used as hydrogenation catalysts for carbohydrates in aqueous solution may be obtained by utilizing carbohydrate feedstocks containing less than about 0.5 ppm dissolved oxygen prior to contact with catalyst under hydrogenation conditions. Using ruthenium as a catalyst, effective lifetime may be doubled with dissolved oxygen levels less than about 0.2 ppm.

9 Claims, No Drawings

INCREASING CATALYST LIFETIME IN HYDROGENATION OF A CARBOHYDRATE IN AQUEOUS SOLUTION

CROSS REFERENCE TO RELATED APPLICATION

This application is a continuation-in-part of my copending application, Ser. No. 457,546, filed Jan. 12, 1983, and now abandoned, all of which is hereby incorporated by reference.

BACKGROUND OF THE INVENTION

A prime consideration in any catalytic process is maximization of the catalyst lifetime. That is to say, it is desirable to have the catalyst perform at or near its optimum efficiency for as long as possible. The process of interest in this application is the catalytic hydrogenation of carbohydrates in aqueous solution.

The discovery leading to the invention described herein is that spent catalyst used in the hydrogenation of a feedstock of glucose in aqueous solution contains gluconic acid, an oxidation product of glucose. Based on this discovery, use of feedstocks low in dissolved oxygen subsequently were shown to lead to substantially increased lifetime of hydrogenation catalysts, thereby affording a considerable improvement over existing processes.

SUMMARY OF THE INVENTION

The purpose of this invention is to lengthen the life of a catalyst employed in the hydrogenation of an aqueous solution of a carbohydrate. In one embodiment the catalyst is a group VIII metal and the feedstock of carbohydrate and aqueous solution contains less than about 0.5 ppm dissolved oxygen immediately prior to its contact with catalyst under hydrogenation conditions. In a more specific embodiment the catalyst is ruthenium.

DESCRIPTION OF THE INVENTION

The invention described herein is an improvement in the method of hydrogenating a feedstock containing a carbohydrate in aqueous solution to its polyols using a group VIII metal as a hydrogenation catalyst, where the improvement comprises using a feedstock containing less than about 0.5 ppm of dissolved oxygen immediately prior to its contact with catalyst under hydrogenation conditions.

Carbohydrates are polyhydroxyaldehydes, polyhydroxyketones, or compounds that can be hydrolyzed to them. A carbohydrate that cannot be hydrolyzed to simpler compounds is called a monosaccharide. One that can be hydrolyzed to two monosaccharide molecules is called a disaccharide, and one that can be hydrolyzed to many monosaccharide molecules is called a polysaccharide. A monosaccharide may be classified according to the number of carbon atoms it contains; a hexose is a 6-carbon monosaccharide, a pentose is a 5-carbon monosaccharide, and a tetrose is a 4-carbon monosaccharide. Monosaccharides are preferred among the carbohydrates which may be used in this invention, and among these the hexoses, pentoses and tetroses are the most important members, with the hexoses particularly preferred.

The polyol reduction products of this invention have the formula $HOCH_2(CHOH)_nCH_2OH$, where n is 2, 3, or 4 depending upon the kind of monosaccharide used or the kind of units in the di- or poly-saccharide. Where n is 4, the polyol is a hexitol; where n is 3, the polyol is a pentitol; and where n is 2, the polyol is a tetritol. It is to be understood that where the carbohydrate is a disaccharide or polysaccharide, substantial hydrolysis accompanies hydrogenation to ultimately afford the polyols of this invention.

The examples of carbohydrates below are cited merely for illustration, and are not intended as exhaustive of the suitable reactants which may be used in this invention. Accordingly, monosaccharides that can be employed include glucose, mannose, galactose, talose, fructose, allose, altrose, idose, gulose, xylose, lyxose, ribose, arabinose, threose and erythrose. Glucose and mannose are particularly preferred monosaccharides which afford sorbitol and mannitol, respectively, as their polyol reduction product. Fructose is another preferred monosaccharide which affords a mixture of sorbitol and mannitol as the product. Examples of disaccharides include maltose, cellobiose, sucrose and lactose. Among the more abundant polysaccharides which may be employed in this invention are starch, cellulose and their degradation products.

Catalysts used for the hydrogenation of carbohydrates include group VIII metals generally. That is, the catalysts used in this invention include iron, cobalt, nickel, ruthenium, rhodium, paladium, osmium, iridium, and platinum. Of these ruthenium seems to be particularly efficacious. The catalyst is used in a dispersed state, sometimes unsupported but more generally supported on an inert carrier. Among such supports are included alumina, silica, various clays, titania, and so forth.

The crux of this invention is that, prior to its being contacted with catalyst under hydrogenation conditions, the feedstock used for hydrogenation and containing the carbohydrate in an aqueous solution contains less than about 0.5 ppm of dissolved oxygen, for such low dissolved oxygen levels lead to improvement in catalyst lifetime. It is preferred that the dissolved oxygen be less than about 0.2 ppm for the best practice of this invention. It is necessary to emphasize that it is essential that the feedstock have the requisite low level of dissolved oxygen prior to contact with the catalyst under hydrogenation conditions; even though one might anticipate that normal hydrogenation procedures would lead to a low level of dissolved oxygen in the feedstock during hydrogenation it is found experimentally that a prior removal of dissolved oxygen leads to improved results.

How the requisite low level of dissolved oxygen is obtained is not critical. One can remove the dissolved oxygen from a feedstock, or one can prepare a feedstock under conditions where it initially contains under about 0.5 ppm oxygen. For example, the feedstock may be purged with hydrogen or an inert gas until the desired oxygen level is obtained. An inert gas is one which has no effect on the feedstock or catalyst, even at hydrogenation conditions. Examples of inert gases include argon, helium, nitrogen. As another example, evacuation or degassing of the feedstock followed by admission of hydrogen or an inert gas may be used to attain the desired low level of oxygen. It may be advantageous to prepare the carbohydrate feedstock in an inert atmosphere to obtain a relatively low initial dissolved oxygen level followed by evacuation and/or purging to attain dissolved oxygen levels less than about 0.5 ppm.

It may be mentioned in passing that mere purging of the headspace of a vessel containing the feedstock normally is insufficient. To reduce the dissolved oxygen level to the stated limit purging requires displacement of the dissolved oxygen, which normally entails either bubbling an inert gas through the feedstock or one or more cycles of evacuation followed by admission of inert gas. It will be recognized by those skilled in the art that conventional procedure entails only purging of the headspace, and therefore is ineffective in obtaining the level of dissolved oxygen necessary for the practice of this invention. Compare U.S. Pat. No. 3,963,788.

After attaining the desired low dissolved oxygen level in the feedstock, hydrogenation is conducted in the usual way. Experimental variables will depend on the carbohydrate being reduced, the nature and concentration of the catalyst used, pressure, temperature, and so on. Hydrogenation conditions, which are well-known to the worker skilled in this art, are not affected by the improvement which is the invention herein; only the results are affected in the context of increased catalyst lifetime. The method of this invention may be advantageously used in either a batch or continuous hydrogenation process, but is especially suited for continuous processes.

The example which follows merely illustrates this invention and is not intended to limit it in any way.

EXAMPLE

Continuous reductions were performed in a ⅜-inch I.D. vertical tube reactor with a spiral preheater and with a bed of 50 cc (32.7 g) catalyst prepared as described below. The same batch of catalyst was used for both feedstocks, which were passed downflow. Hydrogen was introduced at 2300 psig with a hydrogen glucose molar flow ratio of 10:1, the reductions being performed at 120° C. at a liquid hourly space velocity of 1.0. Effluent was analyzed by high pressure liquid chromatography for sorbitol, mannitol, fructose, and glucose. Conversion was measured by the amount of glucose remaining; sorbitol was the major product, with yields of 93% or better.

Catalyst was prepared in the following way. A solution of 11.0 g of $RuCl_3.3H_2O$ in 280 ml of deionized water was mixed with 138 g of theta alumina. Liquid was removed by evaporation with heating, and the impregnated alumina was treated in nitrogen at 400° C. for 3 hours followed by treatment at 400° C. in flowing hydrogen for 3 hours. Analysis of the reduced material showed 3.77% ruthenium.

In run A a 50% aqueous glucose feedstock was prepared by dissolving the appropriate quantity of glucose in deionized water which had been previously heated to 60° C. Vigorous agitation was maintained to effect complete solution, the entire operation being conducted in air. Typical oxygen concentrations of such feedstocks were about 3 ppm. The feedstock was purged by bubbling hydrogen through it prior to use in the continuous reactor, after which oxygen levels were about 1 ppm.

In run B a 50% aqueous glucose feedstock was prepared by dissolving the appropriate quantity of glucose in deionized water at 60° C. with vigorous agitation, the entire operation being conducted under an nitrogen atmosphere. After solution the typical oxygen concentration was about 0.5 ppm. The feedstock was purged by bubbling nitrogen through it prior to use to afford dissolved oxygen levels of about 0.1 ppm. As can be discerned by the differing oxygen levels of the feedstocks used in runs A and B, a deliberate effort must be made to attain dissolved oxygen levels of 0.5 ppm or less. The feedstock of A was prepared so as to attain an oxygen level lower than that of the conventional feedstock prior to hydrogenation (purging was done of the solution, not merely the headspace), yet it still contained more than 0.5 ppm dissolved oxygen.

The relative difficulty in achieving levels of dissolved oxygen under about 0.5 ppm, and the deliberate efforts necessary to obtain such levels, are demonstrated by the following experiment. About 10 liters of feedstock were prepared, as in run A, with a dissolved oxygen level somewhat above 1.0 ppm oxygen. Hydrogen was bubbled through the solution and the oxygen content was monitored with time. The progress of oxygen removed is summarized below.

| Purging Time, Hours | Average Purge Rate in Interval, SCF/Hour | Total Purging Gas at end of Interval, SCF | Dissolved Oxygen, PPM |
|---|---|---|---|
| 0 | | 0 | 1.0 |
| | 1.18 | | |
| 2 | | 2.36 | 1.0 |
| | 1.33 | | |
| 3 | | 3.69 | 0.6 |
| | 2.86 | | |
| 4 | | 6.55 | 0.3 |
| | 1.30 | | |
| 5 | | 7.85 | 0.2 |
| | 0.90 | | |
| 6 | | 8.75 | 0.1 |

These data clearly show that more than 3 hours purging at a substantial purge rate was necessary to bring the dissolved oxygen level under 0.5 ppm, a time which those skilled in the art will recognize as being well outside the realm of usual procedure.

Some results of hydrogenation in runs A and B are given below.

| | CONTINUOUS REDUCTION OF GLUCOSE | |
|---|---|---|
| | % conversion | |
| Time (hours) | feedstock A (1 ppm $O_2$) | feedstock B (0.1 ppm $O_2$) |
| 4 | 99.9 | 99.9 |
| 8 | 99.8 | 99.8 |
| 12 | 99.7 | 99.6 |
| 16 | 99.5 | 99.7 |
| 20 | 99.5 | 99.8 |
| 24 | 99.0 | 99.7 |
| 28 | 99.1 | 99.5 |
| 32 | 99.1 | 99.8 |
| 36 | 98.9 | 99.4 |
| 40 | 98.9 | 99.7 |
| 44 | 99.1 | 99.7 |
| 48 | 98.5 | 99.4 |

As the data show, where the feedstock contains a low level of oxygen glucose conversion remains near 99.5% for at least 48 hours, whereas where the feedstock contains a level of oxygen outside the claims of this invention glucose conversion drops below 99.5% after about 20 hours. From a plot of percent conversion with time, which remained linear over a measuring period of at least 16 days, the rate of catalyst deactivation with feedstock A was about 0.16% per day, whereas that with feedstock B was only about 0.07% per day. Because near quantitative conversion is a commercial imperative these runs show that effective catalyst life can be more than doubled by the invention claimed herein.

What is claimed is:

1. In the method of hydrogenating a feedstock containing a carbohydrate in aqueous solution to its polyols using a group VIII metal as a hydrogenation catalyst, the improvement wherein said feedstock immediately prior to contacting with catalyst under hydrogenation conditions contains less than about 0.5 ppm dissolved oxygen.

2. The method of claim 1 where the metal is selected from the group consisting of iron, cobalt, nickel, ruthenium, rhodium, palladium, osmium, iridium, and platinum.

3. The method of claim 2 where the metal is ruthenium.

4. The method of claim 1 where the carbohydrate is a monosaccharide.

5. The method of claim 4 where the monosaccharide is selected from the group consisting of hexoses, pentoses, and tetroses.

6. The method of claim 5 where the monosaccharide is a hexose and the polyol is a hexitol.

7. The method of claim 6 where the hexose is glucose or mannose and the hexitol is sorbitol or mannitol, respectively.

8. The method of claim 6 where the hexose is fructose and the polyol is a mixture of sorbitol and mannitol.

9. The method of claim 1 where the feedstock contains less than about 0.2 ppm dissolved oxygen.

* * * * *